US00PP17154P3

(12) United States Plant Patent
Kanaya

(10) Patent No.: US PP17,154 P3
(45) Date of Patent: Oct. 17, 2006

(54) ***CALIBRACHOA* PLANT NAMED 'SUNBELPAPI'**

(50) Latin Name: ***Calibrachoa* sp.**
Varietal Denomination: Sunbelpapi

(75) Inventor: Takeshi Kanaya, Omihachiman (JP)

(73) Assignee: Suntory Flowers Limited, Tokyo (JP)

( * ) Notice: Subject to any disclaimer, the term of this patent is extended or adjusted under 35 U.S.C. 154(b) by 226 days.

(21) Appl. No.: 10/814,614

(22) Filed: Mar. 30, 2004

(65) Prior Publication Data

US 2005/0223450 P1 Oct. 6, 2005

(51) Int. Cl.
*A01H 5/00* (2006.01)

(52) U.S. Cl. ..... Plt./263
(58) Field of Classification Search ..... Plt./263, Plt./356
See application file for complete search history.

(56) References Cited

U.S. PATENT DOCUMENTS

PP9,754 P 12/1996 Suzuki et al.
PP10,355 P 4/1998 Murakami
PP11,558 P 10/2000 Murakami
PP15,449 P2 * 12/2004 Pierce ..... Plt./263

FOREIGN PATENT DOCUMENTS

JP PBR 7232 6/1999

OTHER PUBLICATIONS http://www.germaniaseed.com Germania Seed Homepage.*
http://www.germaniaseed.com/pdf/04–747Pinaea.pdf Suntory Collection and Other Specialty Annuals pricelist, Germania Seed Company Jul. 1, 2003.*
http://www.jungpflanzen–gruenewald.de/index2.php?lang=DE&t=produkte&t2=17&t3=167.*
http://216.109.117.135/search/cache?p=sunbelpapi&ei=UTF–8&fl=0&u=www.rhs.org.uk/seedlist/documents/calibrachoa2003.pdf&w=sunbelpapi&d=5D87DCDE30&icp=1&.intl=us Trial o *Calibrachoa*, Vegetatively Propagated, 2003 An Invited RHS Trial.*
UPOV ROM GTITM Computer Databse, GTI Jouve Retrieval Software 2004/06 Citation for 'Sunbelpapi'.*
U.S. Appl. No. 10/723,818, filed Nov. 25, 2003, Murakami. Explanation of Application documents and family documents thereof.

* cited by examiner

*Primary Examiner*—Kent Bell
*Assistant Examiner*—W. C. Haas
(74) *Attorney, Agent, or Firm*—Christie, Parker and Hale, LLP

(57) ABSTRACT

Disclosed herein is a new and distinct variety of *Calibrachoa* plant having an outwardly spreading growth habit. The *Calibrachoa* plant has abundant branching and a great profusion of blooms, the whole plant remaining in bloom for a considerable period of time. The flowers are single and small, the petals having strong purplish pink. The inside color of the corolla throat is vivid yellow and the outside of the corolla tube is light greenish yellow with purplish pink veins. The plant exhibits high resistance to heat, cold, rain and disease.

2 Drawing Sheets

Botanical designation: *Calibrachoa* sp.
Variety denomination: 'Sunbelpapi'.

BACKGROUND OF THE VARIETY

The present invention relates to a new and distinct variety of *Calibrachoa* plant originated from crossing a *Calibrachoa* hybrid variety called '9PP11', as the female parent, and '9CPP8', as the male parent.

The *Calibrachoa* is a popular plant that is used for flower bedding and potting in the summer season. There are only a few *Calibrachoa* varieties known to the inventor, such as 'Sunberubu' (U.S. Plant Pat. No. 9,754), 'Sunbelchipi' (U.S. Plant Pat. No. 10,355) and 'Sunbelki' (U.S. Plant Pat. No. 11,558), which are spreading, and have a medium plant height, with abundant branches and a high resistance to heat, rain and disease. There are even fewer varieties that have a great profusion of flowers, a strong purplish pink color, and high resistance to rain, heat, and disease known to the inventors. Accordingly, the invention was aimed at obtaining a new *Calibrachoa* variety having strong purplish pink and very small flowers, combined with the above features.

The female parent '9PP11' (unpatented) used in the crossing of 'Sunbelpapi' is a strain of our breeding lines grown at Yokaichi-shi, Shiga-ken, Japan, having an outwardly spreading growth habit with abundant branching. It has small single flowers, the petals having a vivid reddish purple color. The flowers of '9PP11' are smaller in size than the flowers of 'Sunbelpapi'.

The male parent '9CPP8' (unpatented) used in the crossing of 'Sunbelpapi' is a strain of our breeding lines grown at Yokaichi-shi, Shiga-ken, Japan, having a decumbent growth habit with abundant branching. It has small single flowers, the petals having a vivid reddish purple color. The growth habit of the male parent, '9CPP8', is decumbent. In contrast, the growth habit of 'Sunbelpapi' is outwardly spreading.

In April 1998, crossing of '9PP11' as the female parent and '9CPP8' as the male parent was conducted at Yokaichi-shi, Shiga-ken, Japan. In September 1998, 50 seedlings were obtained from that crossing. One seedling was selected in view of its growth habit, flower size and color in October 1999. That seedling was propagated by cutting, and the cuttings were grown in field and evaluated from April to September 2000. A trial was carried out by flower potting in the greenhouse and field from April to October 2001 at Yokaichi-shi, Shiga-ken, Japan. The botanical characteristics of that plant were then examined, using similar varieties 'Sunbelchipi' (unpatented) and 'Sunbelkupapi' (unpatented) for comparison. As a result, it was concluded that this *Calibrachoa* plant is distinguishable from any other variety whose existence is known to us, and is uniform and stable in its characteristics. Then the new variety of *Calibrachoa* plant was named 'Sunbelpapi'.

In the following description, the color-coding is in accordance with The R.H.S. Colour Chart.

SUMMARY OF THE VARIETY

This new variety is unlike any *Calibrachoa* commercially available, known to the inventors as evidenced by the following unique combinations of characteristics.

1. Compact and outwardly spreading growth habit with abundant branching.
2. Having a great profusion of blooms with the entire plant remaining in bloom for a considerable period of time.
3. The flowers are single and small. The petal color is strong purplish pink (R.H.S. 75A).
4. The plant has a high resistance to rain, cold, heat and disease.

The new variety 'Sunbelpapi' differs from the similar variety 'Sunbelchipi' in the following points.

1. The plant of 'Sunbelpapi' is more compact than that of 'Sunbelchipi'.
2. The leaf of 'Sunbelpapi' is smaller than that of 'Sunbelchipi'.
3. The leaf shape of 'Sunbelpapi' is elliptic. That of 'Sunbelchipi' is lanceolate.
4. The petal color of 'Sunbelpapi' is strong purplish pink (R.H.S. 75A). That of 'Sunbelchipi' is vivid purplish red (R.H.S. N57A).
5. The outside color of the corolla throat of 'Sunbelpapi' is light greenish yellow (R.H.S. 7D) with purplish pink (R.H.S. N74C) vein. That of 'Sunbelchipi' is brilliant greenish yellow (R.H.S. 5C).
6. The apex shape of the petal of 'Sunbelpapi' is rounded. That of 'Sunbelchipi' is obtuse.
7. The peduncle length of 'Sunbelpapi' is longer than that of 'Sunbelchipi'.

The new variety 'Sunbelpapi' differs from the similar variety 'Sunbelkupapi' in the following points.

1. The growth habit of 'Sunbelpapi' is outwardly spreading. That of 'Sunbelkupapi' is decumbent.
2. The plant height of 'Sunbelpapi' is higher than that of 'Sunbelkupapi'.
3. The leaf of 'Sunbelpapi' is smaller than that of 'Sunbelkupapi'.
4. The leaf shape of'Sunbelpapi' is elliptic. That of 'Sunbelkupapi' is lanceolate.
5. The petal color of 'Sunbelpapi' is strong purplish pink (R.H.S. 75A). That of 'Sunbelkupapi' is deep purplish pink (R.H.S. 73A) with a yellowish white (R.H.S. 115C) eye color.
6. The peduncle length of 'Sunbelpapi' is longer than that of 'Sunbelkupapi'.

This new variety of *Calibrachoa* Plant, 'Sunbelpapi', was asexually reproduced by the use of cuttings at Omori-cho, Yokaichi-shi, Shiga-ken, Japan, and homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during September 2001 while growing in typical outdoor conditions in 24 cm pots, and at an age of approximately 8 months, at Yokaichi-shi, Shiga-ken, Japan. The average day temperature was approximately 23° C. and the average night temperature was approximately 15° C.

DESCRIPTION OF THE VARIETY

Figure 1:
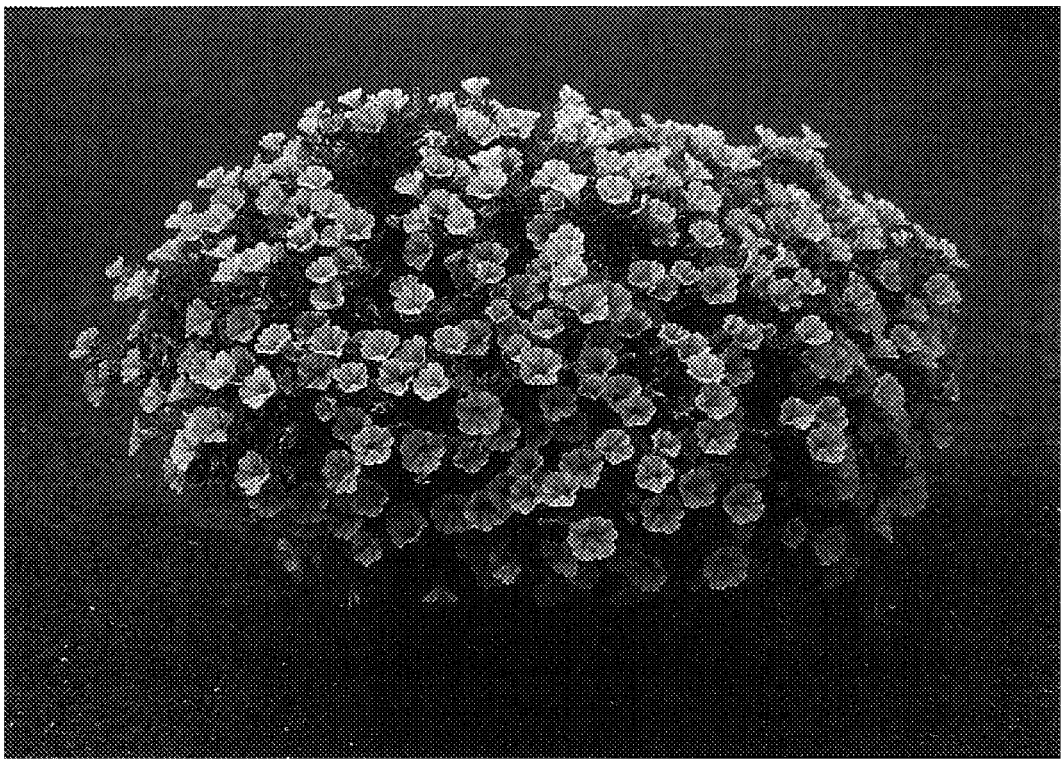
FIG. 1 illustrates a typical plant of the new variety of *Calibrachoa* plant 'Sunbelpapi'.
Figure 2:
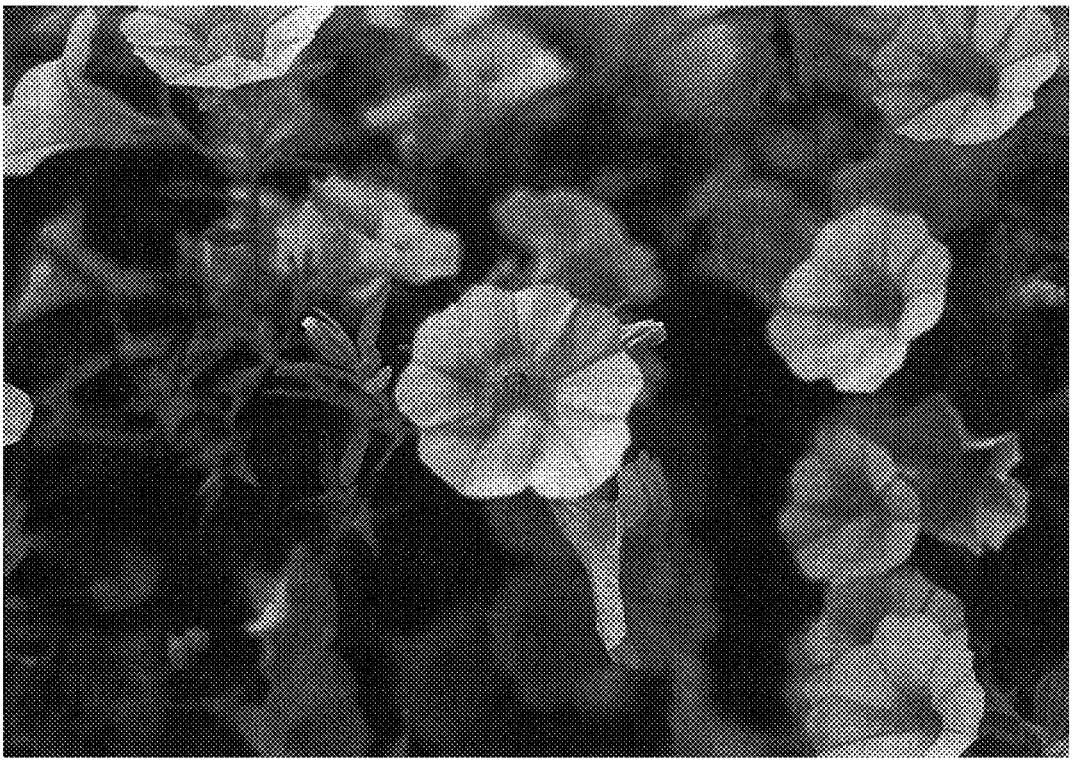
FIG. 2 illustrates a close-up view of typical foliage and blossoms of the new variety of *Calibrachoa* plant 'Sunbelpapi'.

The botanical characteristics of the new and distinct variety of *Calibrachoa* plant named 'Sunbelpapi' are as follows, when observed as grown in typical outdoor conditions during September at Yokaichi-shi, Shiga-ken, Japan at an age of approximately 9 months.

Plant:
- *Growth habit.*—Outwardly spreading.
- *Plant height.*—Approximately 14.6 cm.
- *Spreading area of plant.*—Approximately 45.6 cm.
- *Blooming period.*—April to late October in the southern Kanto area, Japan. The plant shape does not change throughout this period.

Stem:
- *Diameter.*—Approximately 1.3 mm.
- *Pubescence.*—Sparse.
- *Branching.*—Approximately 80 branches per plant.
- *Internode length.*—Approximately 0.6 cm.
- *Color of stem.*—Young — near R.H.S. 144B. Mature — near R.H.S. 200C.

Leaf:
- *Whole shape.*—Elliptic. The apex shape is acute, and the base shape is attenuate.
- *Length.*—Approximately 1.9 cm.
- *Width.*—Approximately 0.8 cm.
- *Color.*—Upper side color is R.H.S. 146A (moderate olive green), bottom side color is R.H.S. 146B (moderate yellow green).
- *Thickness.*—Approximately 0.4 mm.
- *Pubescence.*—Sparse.

Flower:
- *Facing direction.*—Slanted upward.
- *Type.*—Single.
- *Shape.*—Funnel-shape, with five-fissures.
- *Shape of petal tip.*—Rounded.
- *Lobation.*—Shallow.
- *Waving of petal.*—Weak.
- *Diameter.*—Approximately 3.0 cm.
- *Color.*—Petal; Upper Surface, near R.H.S. 75A (strong purplish pink); Lower Surface, near R.H.S. 78B. Inside color of the corolla throat is R.H.S. 14B (vivid yellow). Outside color of the corolla throat is R.H.S.

7D (light greenish yellow) with R.H.S. N74C (purplish pink) vein.

*Reproductive organs.*—1 normal pistil and 5 normal stamens. The stigma is club-shaped and R.H.S. N144D (light yellow green) in coloration. The style is approximately 4.7 mm in length and R.H.S. 145B (brilliant yellow green) in coloration. The ovary is R.H.S. N144D (light yellow green) in coloration. The stamens commonly are of variable length from approximately 4.7 mm to 7.4 mm. Pollen is formed in a quantity that is typical of *Calibrachoa* and is near R.H.S. 21A (vivid orange yellow) in coloration.

*Fertility.*—Fertile, but self-incompatible.

*Peduncle.*—Approximately 0.6 mm in diameter and approximately 4.5 cm in length. The texture is smooth. The color is near R.H.S. 144B.

*Calyx.*—Narrow. 5 sepals fused at the base. Diameter — Approximately 13 mm. Depth — Approximately 10 mm. Color (both surfaces) — near R.H.S. 144B. Texture (both surfaces) — smooth.

*Seeds.*—R.H.S. N186A (strong red) in coloration, approximately 0.6 mm in diameter, and generally spherical. The quantity is typical of *Calibrachoa*.

Physiological and ecological characteristics: High resistance to cold, heat, rain and disease such as Powdery mildew. The resistance to heat and rain is very strong. Low temperature tolerance is at least 5° C.; high temperature tolerance is approximately 35° C.

This new variety of *Calibrachoa* plant is most suitable for flower bedding and potting, particularly in hanging pots or planters. Pinching of old blossoms will enhance the formation of new blossoms.

It is claimed:

1. A new and distinct variety of *Calibrachoa* plant named 'Sunbelpapi', substantially as herein illustrated and described.

* * * * *